(12) United States Patent
Peterson (10) Patent No.: US 7,413,622 B2
(45) Date of Patent: *Aug. 19, 2008

(54) METHOD OF TRAINING NITINOL WIRE

(75) Inventor: Francis Peterson, Spooner, WI (US)

(73) Assignee: ev3 Inc., Plymouth, MN (US)

( * ) Notice: Subject to any disclaimer, the term of this patent is extended or adjusted under 35 U.S.C. 154(b) by 501 days.

This patent is subject to a terminal disclaimer.

(21) Appl. No.: 10/951,327

(22) Filed: Sep. 27, 2004

(65) Prior Publication Data

US 2005/0061406 A1   Mar. 24, 2005

Related U.S. Application Data

(63) Continuation of application No. 10/167,042, filed on Jun. 11, 2002, now Pat. No. 6,797,083.

(60) Provisional application No. 60/296,727, filed on Jun. 11, 2001.

(51) Int. Cl.
*C22F 1/10* (2006.01)
(52) U.S. Cl. ....................... 148/563
(58) Field of Classification Search .......... 148/563
See application file for complete search history.

(56) References Cited

U.S. PATENT DOCUMENTS

| | | | |
|---|---|---|---|
| 3,985,177 A | 10/1976 | Buehler | |
| 4,435,229 A | 3/1984 | Johnson | |
| 4,753,689 A | 6/1988 | Rizzo et al. | |
| 4,758,285 A | 7/1988 | Hodgson et al. | |
| 4,789,410 A | 12/1988 | Parizek | |
| 4,904,048 A * | 2/1990 | Sogawa et al. | 385/118 |
| 5,120,175 A | 6/1992 | Arbegast et al. | |
| 5,388,869 A * | 2/1995 | Suzuki et al. | 285/197 |
| 5,607,756 A | 3/1997 | Yamauchi et al. | |
| 5,669,991 A | 9/1997 | DeFilippo | |
| 5,725,552 A | 3/1998 | Kotula et al. | |
| 5,901,775 A | 5/1999 | Musschoot et al. | |
| 5,944,738 A | 8/1999 | Amplatz et al. | |
| 5,997,526 A | 12/1999 | Giba et al. | |

(Continued)

FOREIGN PATENT DOCUMENTS

JP   03-140445 A   6/1991

(Continued)

OTHER PUBLICATIONS

Search Report for counterpart PCT application PCT/US02/19155.

(Continued)

*Primary Examiner*—George Wyszomierski
(74) *Attorney, Agent, or Firm*—Popovich, Wiles & O'Connell, P.A.

(57) ABSTRACT

A method of coating a pre-formed trainable material, such as nitinol wire, with a heat resistant substance, heat treating, and cooling to form a desired shape. The substance can be removed by various methods after heat treatment, depending upon the composition of the substance. The method includes forming a trainable material around a mold that dissolves, vaporizes, or can otherwise be removed. The method is useful for forming complicated shapes that would be expensive or impossible to form by conventional methods.

65 Claims, 12 Drawing Sheets

U.S. PATENT DOCUMENTS

| | | | |
|---|---|---|---|
| 6,106,642 | A | 8/2000 | DiCarlo et al. |
| 6,123,715 | A | 9/2000 | Amplatz |
| 6,129,135 | A | 10/2000 | Divecha et al. |
| 6,210,500 | B1 | 4/2001 | Zurfluh |
| 6,240,978 | B1 | 6/2001 | Gianotti |
| 6,267,402 | B1 | 7/2001 | Julien |
| 6,279,368 | B1 | 8/2001 | Escano et al. |
| 6,368,339 | B1 | 4/2002 | Amplatz |
| 6,383,196 | B1 | 5/2002 | Leslie et al. |
| 6,602,271 | B2 | 8/2003 | Adams et al. |
| 6,797,083 | B2 * | 9/2004 | Peterson ............... 148/563 |
| 6,986,855 | B1 * | 1/2006 | Hood et al. ............ 264/219 |
| 2002/0004667 | A1 | 1/2002 | Adams et al. |
| 2002/0045916 | A1 | 4/2002 | Gray et al. |

FOREIGN PATENT DOCUMENTS

| | | |
|---|---|---|
| WO | WO 94/06372 | 3/1994 |
| WO | WO 96/01591 | 1/1996 |
| WO | WO 99/39646 | 8/1999 |
| WO | WO 01/21246 A1 | 3/2001 |
| WO | WO 01/89413 A2 | 11/2001 |

OTHER PUBLICATIONS

European Search Report dated Aug. 31, 2004 for the counterpart European Application No. EP 02 74 7902 (3 pages).

Hebda et al., "Effect of Training Conditions and Extended Thermal Cycling on Nitinol Two-Way Shape Memory Behavior," *Smart Materials and Structures*, 4(4):298-304 (1995).

Hebda et al., "Manufacturing of Adaptive Graphite/Epoxy Structures With Embedded Nitinol Wires," *Journal of Intelligent Material Systems and Structure*, Mar. 1995 (abstract) (1 page).

* cited by examiner

METHOD OF TRAINING NITINOL WIRE

This Application is a continuation of application Ser. No. 10/167,042, filed Jun. 11, 2002 now U.S. Pat. No. 6,797,083, which claims benefit to provisional application U.S. Ser. No. 60/296,727 filed in the U.S. Jun. 11, 2001.

FIELD OF THE INVENTION

This invention relates to a method for training nitinol wire, particularly the training of nitinol wire into complicated shapes that would be expensive or impossible by conventional methods.

BACKGROUND OF THE INVENTION

Nitinol, a nickel-titanium alloy, is well known in the art for its superb elasticity. Nitinol wire and wire mesh can be permanently formed into a desired shape by a process called training. Training consists of first manually manipulating the trainable material into the desired shape and then heat treating it while holding it firmly in that shape. The heat treatment consists of subjecting the material to a high temperature for a particular amount of time and then cooling it. For nitinol, this high temperature is usually between about 450 and 600° C., and this time usually ranges from a few seconds to three minutes. After the nitinol is subsequently cooled, it will maintain the desired shape.

Methods of heat treating are well known in the art. Heat treating a material requires a uniform rate of heating and cooling to minimize undesired stresses on the material. A method of heat treating and quenching complex geometries without distortion or cracking is taught in U.S. Pat. No. 4,789,410 by Parizek. It teaches the use of two salt baths held at different temperatures into which the material to be treated is submerged at different times.

During the heat treatment, the nitinol must be held firmly in its desired shape, otherwise the shape of the nitinol will warp during the heat treatment. In order to overcome this warping and to provide a firm support for the nitinol during heat treatment, the standard method of forming nitinol into a desired shape is to first create a metal mold that can withstand a high temperature. The mold consists at least of a first piece and a second piece, the first piece able to fit snugly into the second piece, and the two pieces able to lock together. The nitinol in a wire or wire mesh form is then sandwiched between the two pieces and then the pieces are pressed and locked together, thus giving the nitinol the desired shape. The entire mold with the nitinol inside is then subjected to the heating process. For more complicated shapes, more than two pieces may be used, but in each case every part of the nitinol is sandwiched between at least two of these pieces and remains sandwiched during the heating process.

Another method of reducing warpage during the heat treatment is taught in U.S. Pat. No. 6,210,500 by Zurfluh. It teaches a fixture that has porous support walls that engage opposite sides of the material to be heat treated. A liquid heating and cooling media is then flowed through the porous walls to heat treat the material while the support walls minimize warpage of the material.

One problem with conventional methods is that they are not conducive to certain shapes. For example, shapes that have an enclosed volume cannot be easily formed using the conventional methods. This is because once the heat treatment has taken place, it is not possible to remove a solid metal mold from inside. One way to solve this problem is by using a collapsible inside mold, but this method is very expensive and complicated. Another problem with this method is that some complicated shapes are not even conducive to such collapsible molds.

Another way to solve the problem of training materials into complicated shapes is by using a mold that is created from sand bound by a resin binder. The material can then be shaped around the sand mold and heat treated with the sand still inside. After the heat treatment, the sand mold can be broken down and removed, for example, by vibration. A means for processing and reusing sand molds is described in U.S. Pat. No. 5,901,775 by Musschoot et al.

One problem with such a method is that the sand mold is very crude and the resulting trained material must be processed or machined in order to remove the roughness and imperfection resulting from the sand mold. Another problem is that the external part of the mold, made of metal or sand (depending on the application) is bulky and heavy. This results in three further problems: high expense of the external mold; high expense of continually heating and cooling mold materials; high expense of large heat treating baths or ovens and processing equipment; difficulty in achieving a uniform rate of heating and cooling due to the thickness of the external part of the mold. This makes the cooling process and cooling rate harder to control. The cooling rate must be carefully controlled. Nitinol must be cooled to a point at which it retains the desired shape without the support of the mold, but if it is cooled too quickly, it can become unacceptably brittle.

SUMMARY OF THE INVENTION

One object of the present invention is to overcome the disadvantages of the known art described above.

Another object of the present invention is to provide a method of training a heat settable or trainable material such as nitinol in a desired shape which does not warp or change shape during the heat treatment process.

Another object of the present invention is to provide a method of training nitinol in complicated shapes.

Another object of the present invention is to provide a method of training nitinol in a desired shape that includes at least one hole or core through which a solid mold cannot exit.

Another object of the present invention is to provide a method of training nitinol inexpensively and without the use of heavy, expensive molds.

The present invention provides a method of training a trainable material, comprising the steps of forming the material into a desired shape, applying a heat-resistant substance to the material capable of holding the material in the desired shape, heating the material to a temperature and time sufficient for the material to retain the shape, cooling the material, and removing the substance from the material. In a preferred aspect, the material permanently retains its shape after removing the substance from the material, and the material comprises a nickel titanium alloy, such as a nitinol alloy. In another preferred aspect, the substance remains in a solid form at the temperature, and comprises one of plaster of paris, concrete, a ceramic, paint, and glue. A preferred time and temperature are, respectively, greater than one second and less than about 10 minutes, and greater than about 450° C. and less than about 600° C. In another preferred aspect, the cooling step comprises cooling with the use of a gas, such as air or compressed air, or with the use of a liquid, such as water.

In another preferred aspect, the step of forming the material comprises forming the material with a mold comprising a plastic, such as an ethylene, that has been created by injection molding. In another preferred aspect, the step of removing the substance comprises dissolving the substance in a dissolving substance, e.g., water. In another preferred aspect, the step of removing the substance comprises one of chemically reacting the substance with a reacting substance and breaking the substance—e.g., by vibrating the substance.

The present invention also provides a method of training a trainable material, comprising the steps of forming a mold of a desired shape, forming the material with the use of the mold, applying a heat-resistant substance to the material capable of holding the material in the desired shape, heating the material to a temperature and time sufficient for the material to retain the shape, cooling the material, and removing the substance from the material. In a preferred aspect of the present invention, at least part of the mold is removed prior to heating the material. In another preferred aspect, the material permanently retains its shape after removing the substance from the material, and the material comprises a nickel titanium alloy, such as a nitinol alloy. In yet another preferred aspect, the heat-resistant substance is in a non-solid form that hardens after application, and remains in a solid form at the temperature, and comprises one of plaster of paris, concrete, a ceramic, paint, and glue. A preferred time and temperature are, respectively, greater than one second and less than 10 minutes, and greater than about 450° C. and less than about 600° C. In another preferred aspect, at least a part of the mold is retained after applying the heat resistant substance and is pyrolyzed during the heating of the material. In another preferred aspect, the cooling step comprises cooling with the use of a gas, such as air or compressed air, or with the use of a liquid, such as water.

In another preferred aspect, the step of heating the material comprises heating at least one piece of the mold, and the piece vaporizes at a vaporization temperature below the temperature, and the piece vaporizes completely. In another preferred aspect, the step of forming the material comprises forming the material with a mold comprising a plastic, such as an ethylene, that has been created by injection molding. In another preferred aspect, the step of removing the substance comprises dissolving the substance in a dissolving substance, such as water. In another preferred aspect, the step of removing the substance comprises one of chemically reacting the substance with a reacting substance and breaking the substance—e.g., by vibrating the substance. In another preferred aspect, the piece is removed from the material, and it is removed by one of dissolving the piece in a mold dissolving substance, such as water, chemically reacting the piece in a mold reacting substance, and breaking the piece—e.g., by vibrating the piece. In another preferred aspect, the step of removing the substance and removing the piece occur at substantially the same time.

These objects and advantages, as well as other objects and advantages, of the present invention will be set forth in the description that follows, and in part will be readily apparent to those skilled in the art from the description and drawings, or may be learned by practice of the invention.

DETAILED DESCRIPTION OF PREFERRED EMBODIMENTS

The present invention avoids the above problems by providing a method of coating a pre-formed trainable material with an inexpensive heat-resistant substance that can be removed after the heat treatment. The present invention also provides a method of forming a trainable material around a mold that can either vaporize during the heat treatment or can be removed after the heat treatment.

The present invention is usable with any material that can be formed into a desired shape and then set or trained by heat. While the following preferred embodiments have been described with respect to nitinol and its alloys, it should be understood that other materials, such as steel and spring wire, are within the scope of the invention.

The present invention relates to a method for training nitinol wire, particularly the training of nitinol wire into complicated shapes that may be expensive or impossible by conventional methods.

In a preferred embodiment, a practice of the method of the invention begins with forming a trainable material into a desired shape. In this embodiment, the trainable material is nitinol, a nickel-titanium alloy, but the practice of this method on other trainable materials will be apparent to one skilled in the art. The nitinol can be in the form of a wire, a wire mesh, braided wire, a sheet, a tube, a slotted tube, or any other form that can be manipulated into a desired shape. The forming of the nitinol can be accomplished in any number of ways. In the most basic embodiment, the nitinol can be formed by hand into a desired shape. One skilled in the art will recognize the many possible apparatuses available to form a wire or sheet into a desired shape. In a preferred embodiment, a mold is initially used to form the nitinol into the desired shape. Because of the inherent elasticity of nitinol, the nitinol will spring back into its trained shape unless held in the desired shape throughout the training process.

The nitinol is held in its desired shape with the use of a preferably non-solid heat-resistant substance that hardens with time. Examples of such a substance include plaster of paris, concrete, cement, and ceramics, although similarly useful substances would be apparent to one skilled in the art. Other examples include resins, glues, adhesives, paints, and varnishes. The heat-resistant substance is then applied either when or after the mold is applied to the nitinol. More than one coat of the substance can be applied, and the thickness of each coat may vary, depending on the strength required to hold the nitinol in its desired shape. After the substance hardens, the substance will hold the nitinol in the desired shape, and the mold can be removed from the nitinol prior to the heat treatment step. In this embodiment, it is the mold that forms the nitinol into its desired shape, and the heat-resistant substance that holds the nitinol in its desired shape after the mold has been removed.

One advantage of the present invention is the ability to form the nitinol first, and then to hold it in place for the heat treatment step. In conventional methods, the forming and holding takes place at the same time and with the same implement, such as a mold. While a mold could be used with the present invention to initially form the nitinol, the forming step is independent of the holding step. Therefore, the implement that was used to form the nitinol (e.g., a mold) does not necessarily enter the heat treatment step with the nitinol. It will be apparent to one skilled in the art that many other implements could be used to form the nitinol.

In a preferred embodiment, a mold made of an injection molded piece of polyethylene is used to form the nitinol. Injection molding is an inexpensive, efficient process that creates precision molds, and polyethylene is an inexpensive, easy-to-use plastic. However, it would be apparent to one skilled in the art that many other possible materials and mold-creating methods could be used to create the mold. A mold could, for example, be created out of a metal, ceramic, or another suitable plastic.

The mold consists at least of a first piece and a second piece, the first piece able to fit snugly into the second piece, and the two pieces are able to fit together and may lock together. Also, one or both of the pieces must contain ribs, channels, or other spaces so that, when they are locked together, there is sufficient space for both the nitinol and the heat-resistant substance. The nitinol, preferably in a wire or wire mesh form, is then sandwiched with the heat-resistant substance between the two pieces and then the pieces are pressed and locked together, thus giving the nitinol the desired shape. For more complicated shapes, more than two pieces may be used. Preferably, in each case, every part of the nitinol is sandwiched with the heat-resistant substance between at least two of these pieces. However, in some instances, part of the nitinol may remain free of the mold.

In this embodiment, the heat-resistant substance is then allowed to harden, and then the mold is removed from the nitinol. The nitinol is then held in its desired shape by the heat-resistant substance that has hardened around it.

In another embodiment, the nitinol is formed by some means other than the mold mentioned, and then it is dipped into the heat-resistant substance which is subsequently allowed to harden. For example, in order to form a nitinol wire mesh into a flat sheet and hold it in this shape for heat treating, a nitinol wire mesh could be stretched out over a hard surface, each of its corners attached to the surface by conventional means such as a clip or screws. The entire surface could then be dipped in the heat-resistant substance, or the heat-resistant substance could be poured or sprayed onto the surface. When the substance hardened, the substance-coated nitinol could then be detached from the surface by removing the clips or screws. The nitinol would then be held in its desired shape by the heat-resistant substance and ready to be heat treated.

In a preferred embodiment, the substance-coated nitinol is then subjected to a heat treatment, whereby the nitinol is heated to a temperature at which the nitinol is trained. At this temperature, the nitinol loses its elasticity and assumes the desired shape without resistance. The temperature at which this happens is approximately 530° C., although it can happen in the approximate range of about 450° C. to about 600° C. In this embodiment, the heat-resistant substance remains in solid form at this temperature, continuing to hold the nitinol in the desired shape. The nitinol is then held at this temperature for enough time to allow the nitinol to assume its desired shape, and then it is cooled. The required amount of time generally ranges from about one second to ten minutes, with anything beyond ten minutes generally being unnecessary. The cooling of the nitinol is required to allow it to achieve elasticity. The cooling rate should be fast enough that the process is efficient and not wasteful of time. However, if the cooling rate is too fast, thermal stresses arise in the nitinol that cause it to be brittle. Because of the benefits of the nitinol's superelasticity, embrittlement should be avoided. One skilled in the art of training materials such as nitinol can readily determine suitable cooling times and temperatures.

The cooling can take place with the use of many possible heat transfer media. The type of media used will depend on the complexity and size of the desired shape, and also the thickness of the heat-resistance substance layer on the nitinol, because the heat-resistance substance may be an insulator. In the conventional method of heat treatment, a very dense, conductive heat transfer medium is used because the molds are usually very thick. However, because the heat-resistant substance layer can be very thin in comparison to conventional molds, the heat transfer rate through such a layer may be much higher than in conventional molds. For this reason, a heat transfer medium that is low in density or heat conductivity may be useful in the cooling process. In a preferred embodiment, the heat transfer medium for cooling process is air or compressed air. Air is inexpensive, compared to a salt bath, for example. In another preferred embodiment, water is used as the cooling medium, because it has a high heat transfer rate. Water is used when the heat-resistant substance is thick, in order to increase efficiency of the method, but care should be taken to make sure the nitinol is not embrittled by the faster cooling rate of water. Many other possible gaseous or liquid heat exchange media for the cooling process will be apparent to one skilled in the art.

After the cooling process, the heat-resistant substance is removed. The substance can be removed in many different ways. In one embodiment, the substance is removed by dissolving it in a dissolving medium, such as water. For example, the substance-coated nitinol can simply be dipped in a bath of water, or water can be sprayed on to the substance-coated nitinol until the substance is completely removed. Other dissolving media can be used, but care should be taken that there is no reaction between the dissolving medium and the nitinol itself unless, of course, such reaction is desired. Water works well, for example, in dissolving plaster of paris.

In another embodiment, the substance is simply broken off of the nitinol. This breaking process can be accomplished in many ways that will be apparent to one skilled in the art. For example, the substance-coated nitinol can be struck with a hammer-type or wedge-type tool. Because the heat-resistant substance is brittle but the nitinol is elastic, this method of breaking the substance will cause the substance to shatter with the nitinol remaining intact. Another example is the use of vibrations to break the substance. The substance-coated nitinol can be subjected to intense, high-frequency sound waves in a gas or liquid medium, causing the brittle heat-resistant substance to be pulverized. Again, the elastic nitinol will remain intact.

In another embodiment, the heat-resistant substance is removed by chemical reaction with a chemical reacting substance. The application of such a reacting substance is similar to the application of a dissolving substance, discussed above, and care should be taken that there is no reaction between the reacting substance and the nitinol itself unless a reaction is desired.

In another preferred embodiment, the nitinol is first formed with the use of a mold. The heat-resistant substance is applied either during or after the application of the mold to the nitinol, as discussed previously. However, instead of removing all pieces of the mold, at least one piece of the mold remains with the substance-covered nitinol through at least part of the heat treating process and, if necessary, is removed after the heat treating process. This embodiment is useful when the desired shape has at least one enclosed volume through which a solid mold would not be able to exit after the heat treating process.

Referring to FIGS. 1 to 12, all of the objects have shapes that would not be easily formed with conventional means. For example, FIGS. 1 to 7 show various shapes that are convoluted or have enclosed volumes. If a solid mold piece had been used on the inside of the object, that piece would have been difficult or impossible to remove after the heat treating process without breaking or tearing the object open. In such embodiments, as described below, where at least a part of the mold remains prior to heating and is destructively removed during heating such as by pyrolysis or after heating such as by dissolution or mechanical destruction the remaining mold/mold piece is considered to be a "sacrificial mold."

Figure 1:
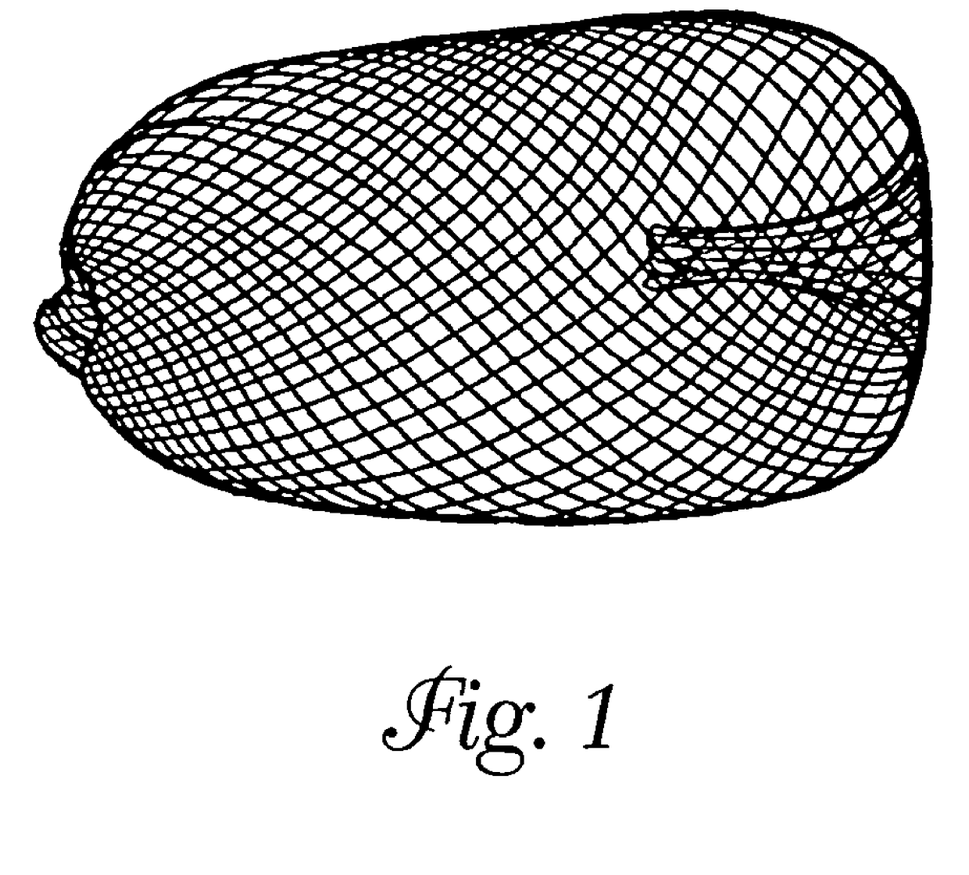
FIGS. 1 to 6 show nitinol wire structures formed by the method of the invention.

FIG. 1 shows tubular material trained into a closed ended cylinder with both ends folded inwardly into the interior of the closed cylinder. The ends of the braided material are substantially gathered so as to minimize the passageway from the interior of the structure to the exterior of the structure.

Figure 2:
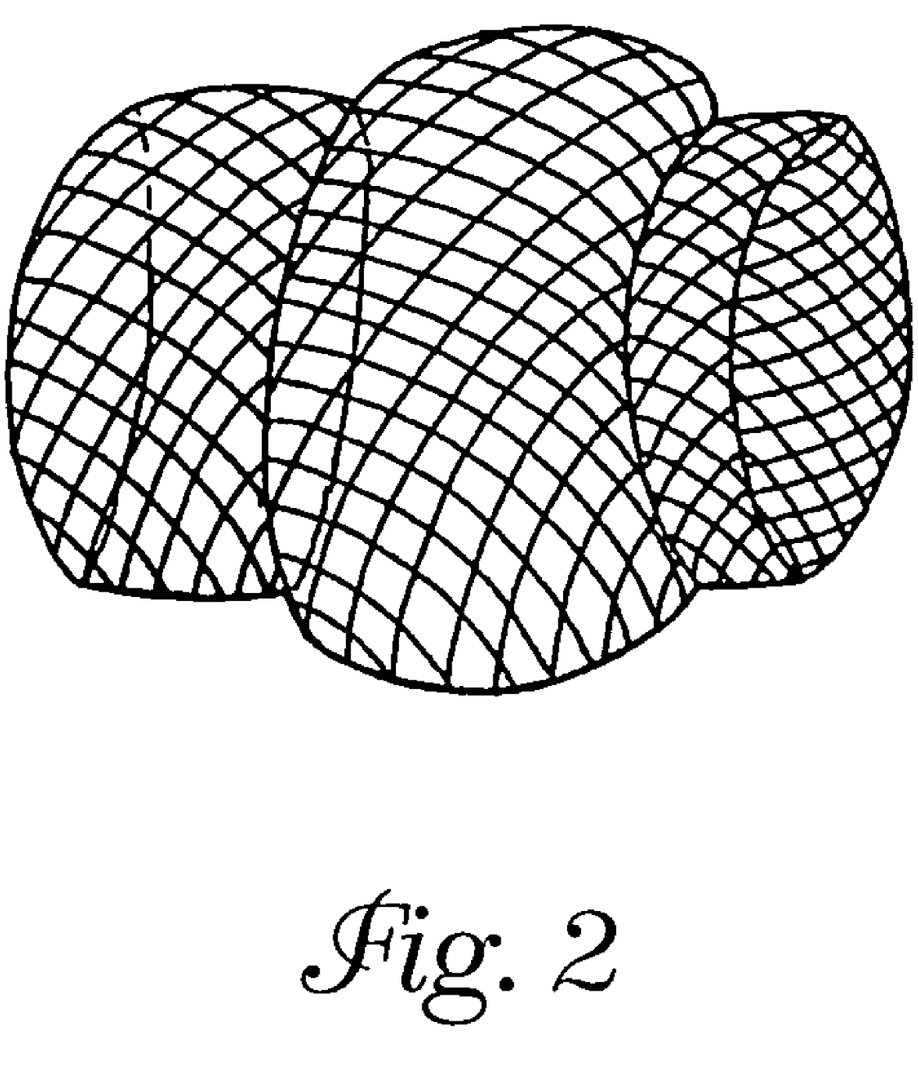
Figure 10:
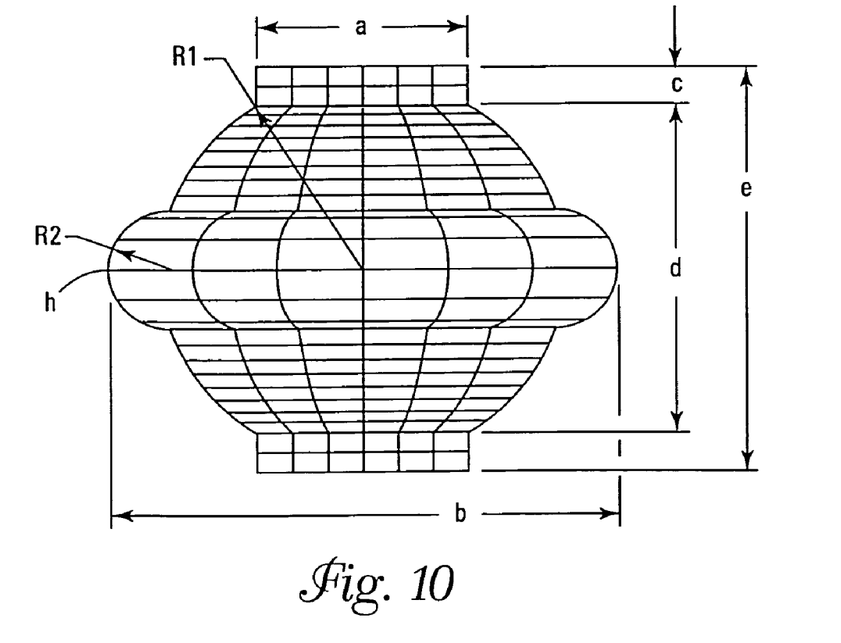

FIG. 2 shows the structure dimensioned in FIG. 10. FIG. 2 shows tubular material trained into a cylindrical tube of mesh material with a spherical bulge along the axis of the tubular mesh material.

Figure 3:
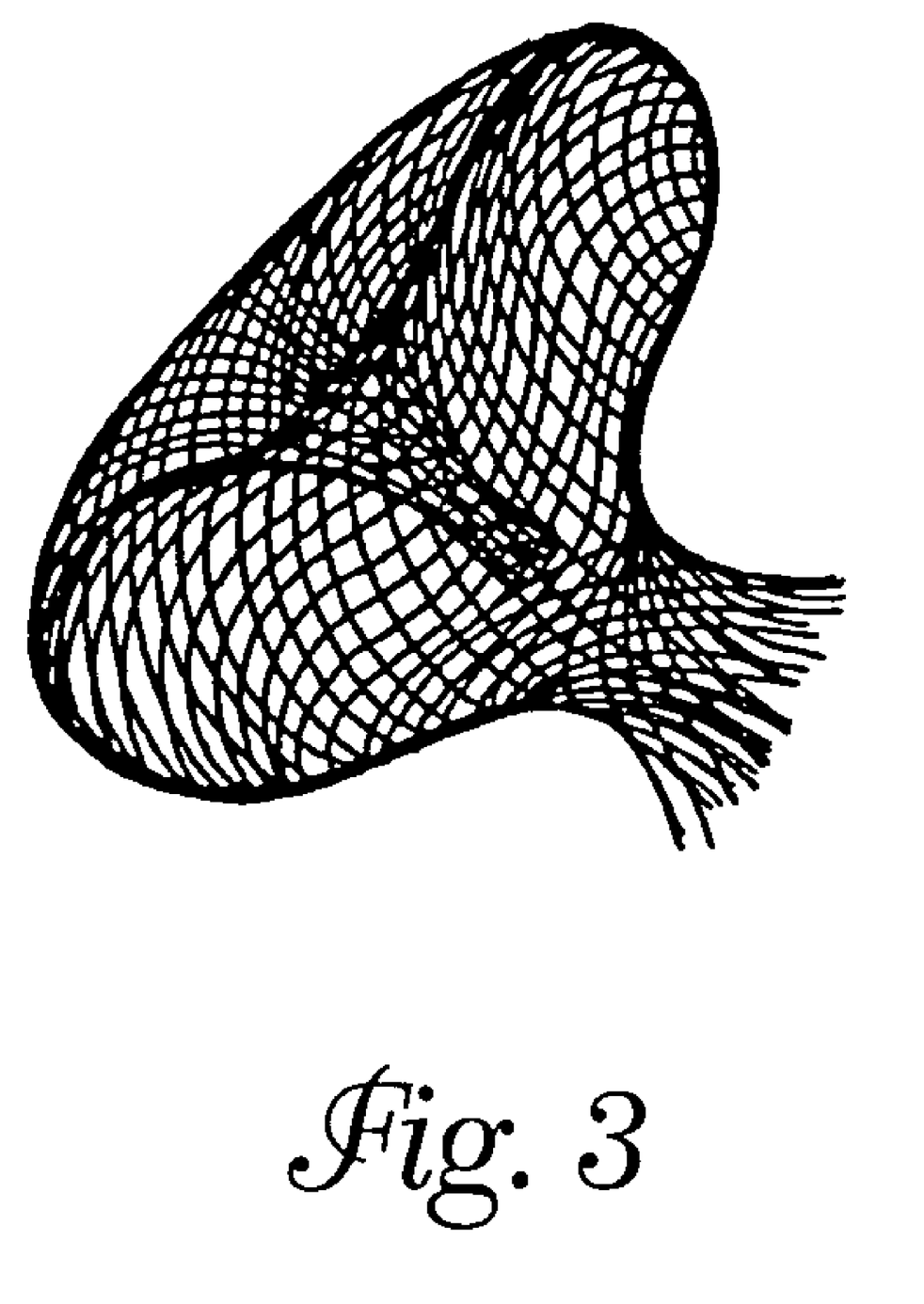

FIG. 3 shows tubular material trained into a spheroid shape with one end of the tube folded inwardly into the interior of the spheroid and the opposite end of the tubular material trained into a loosely gathered configuration external to the spheroid shape.

Figure 4:
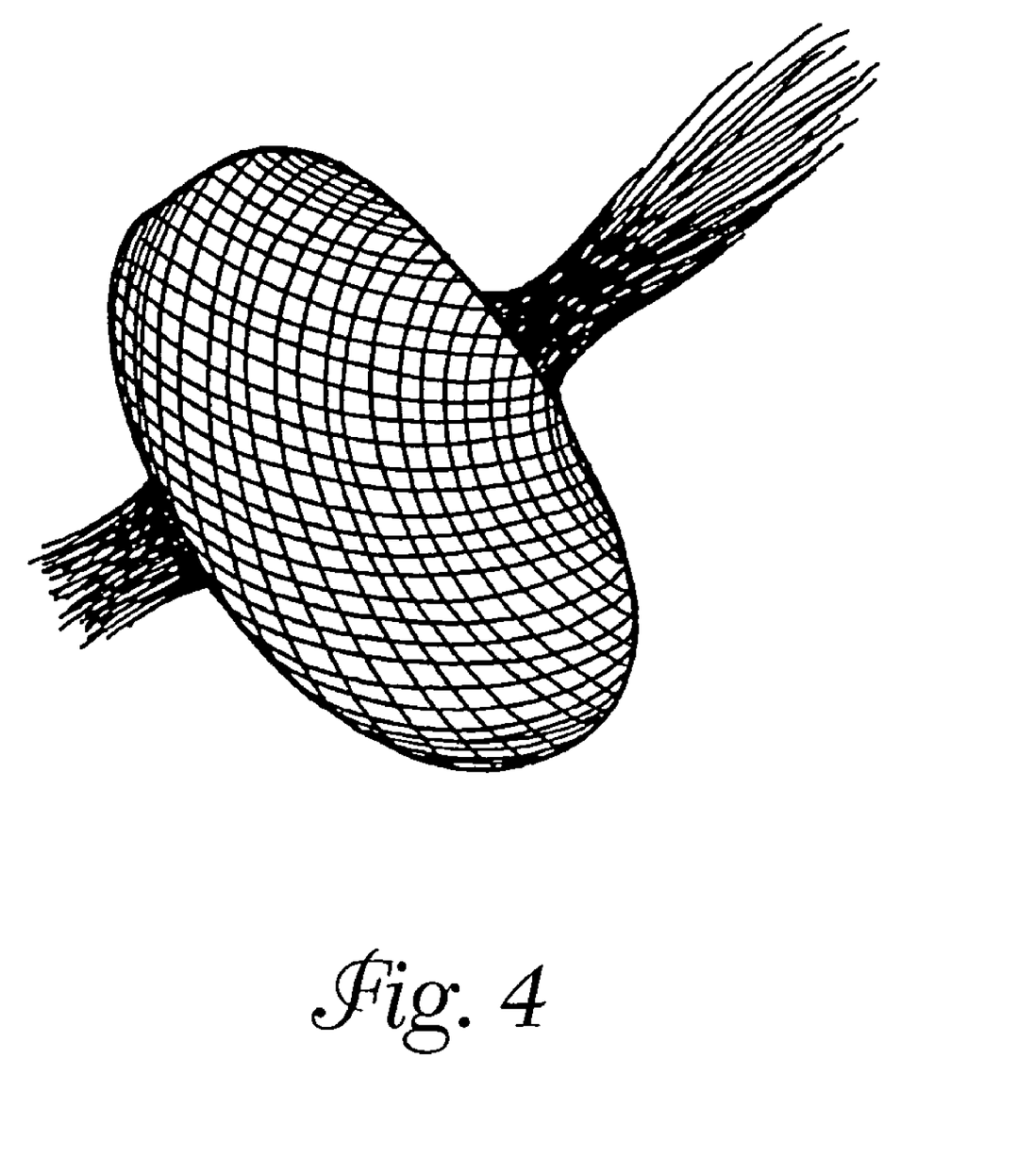

FIG. 4 shows tubular material trained into a spheroid shape with both ends of the tubular material trained into loosely gathered configurations external to the spheroid shape.

Figure 5:
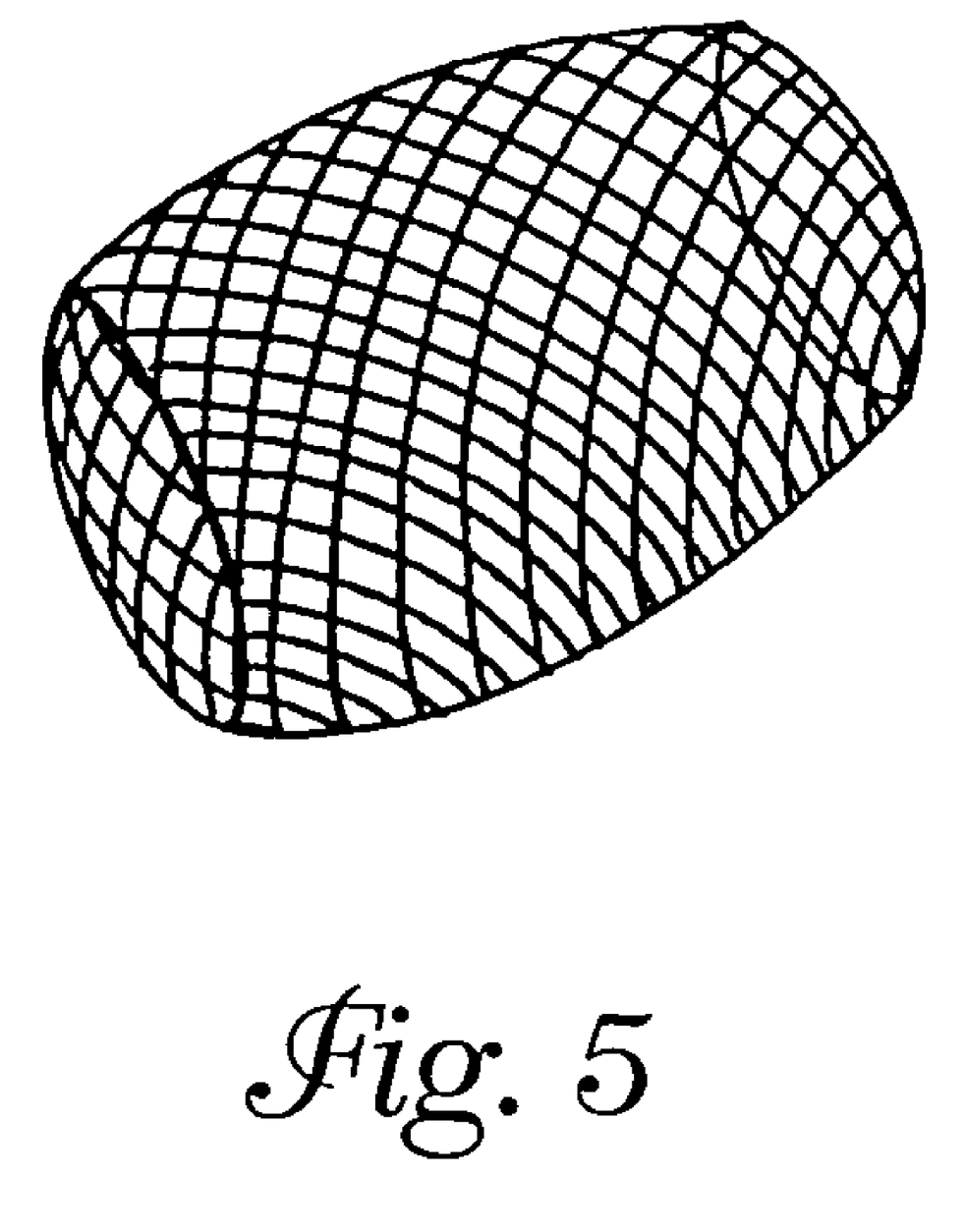

FIG. 5 shows a cut length of tubular material trained into a cylindrical open ended cylinder with both cut ends folded inwardly into the interior of the cylinder and expanded to lie against the interior wall of the open cylinder. The length of the open cylinder has been trained to assume a curvilinear shape with the open ends of the cylinder smaller in diameter than the midlength transverse diameter of the cylinder.

Figure 6:
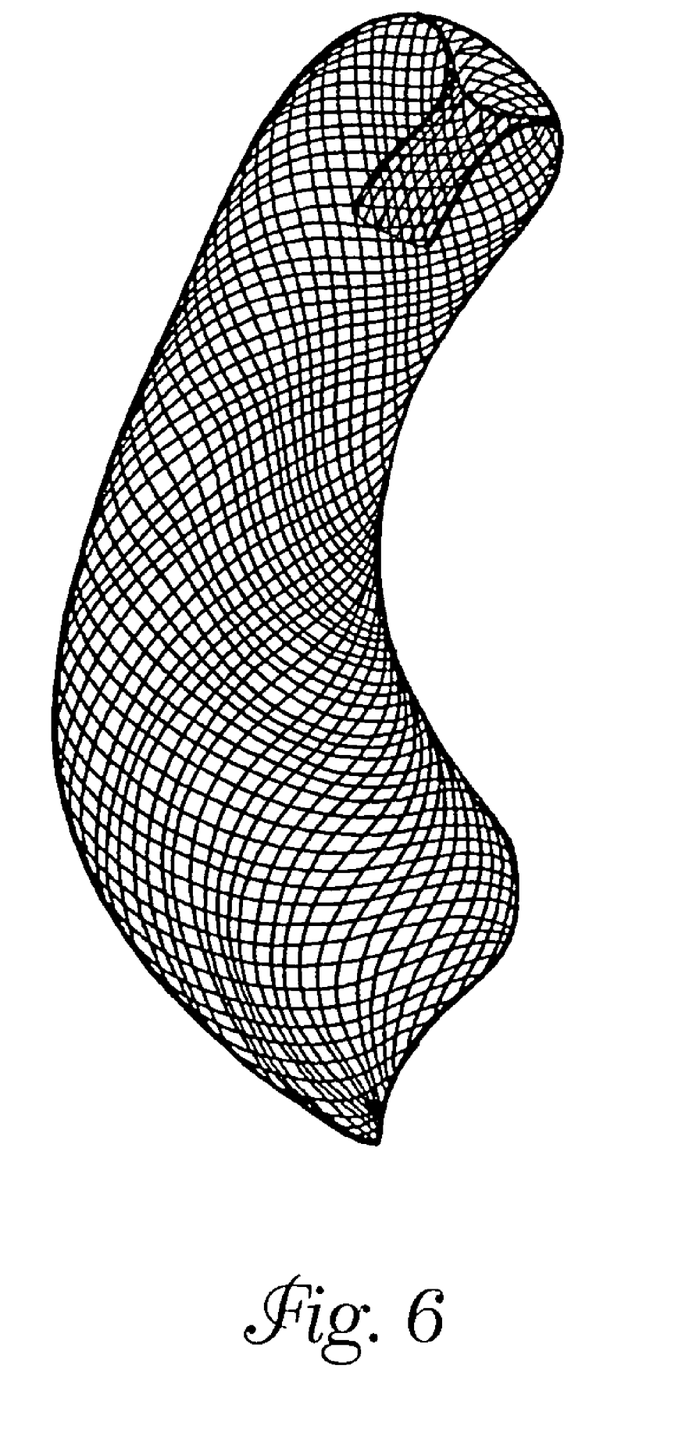

FIG. 6 shows a cut length of tubular material trained into a substantially closed ended cylinder with both cut ends folded inwardly into the interior of the cylinder and with both ends of the tubular material trained into loosely gathered configurations. One of the inwardly folded ends is substantially coaxial with the end perimeter of the closed ended cylinder and the opposite inwardly folded end is substantially eccentric to the end perimeter of the closed ended cylinder. The length of the cylinder has been trained to assume a curvilinear shape with one end of the cylinder smaller in diameter than the opposite end of the cylinder.

Figure 7:
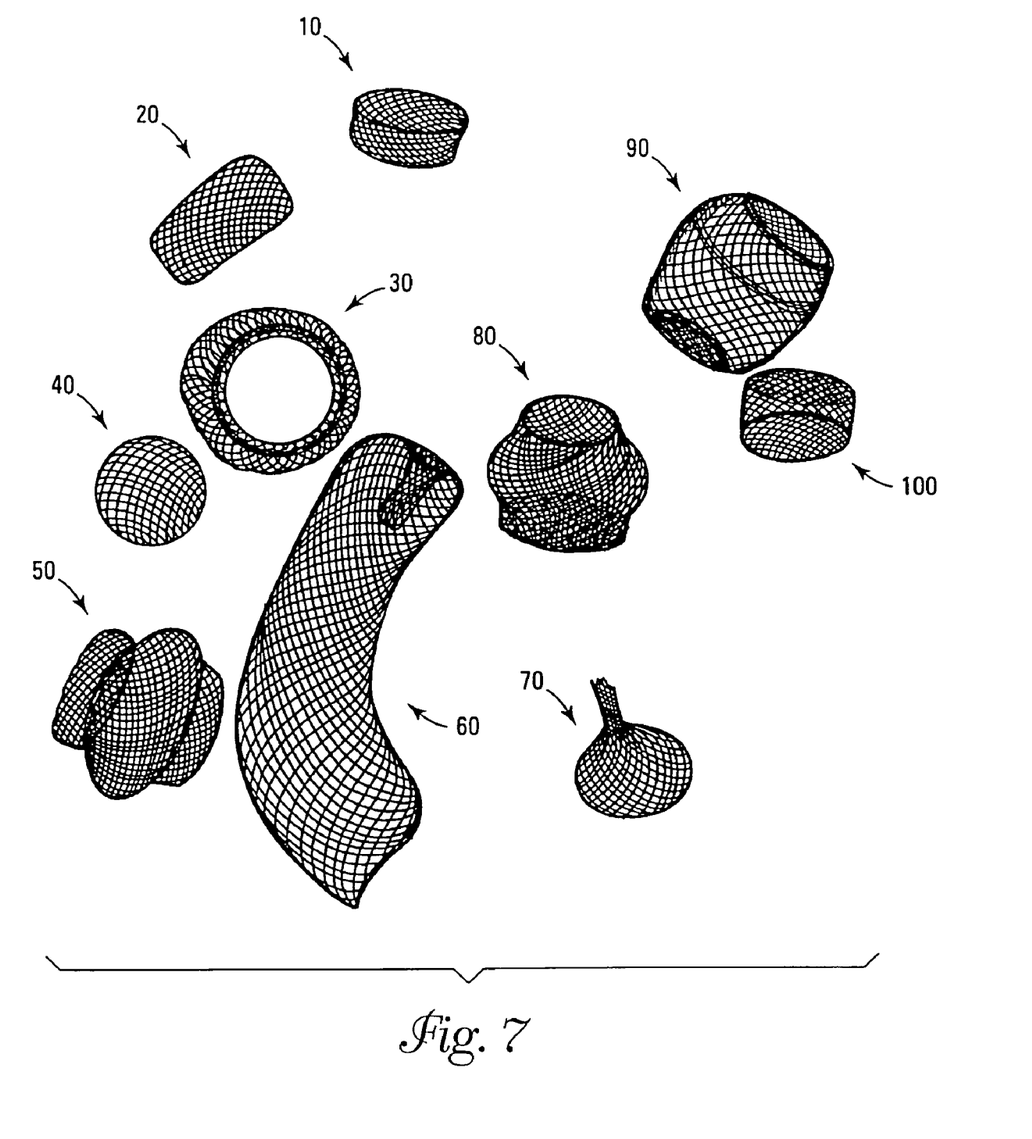
FIG. 7 shows a collection of nitinol wire structures and their relative sizes.

FIG. 7 illustrates objects 10, 20, 30, 40, 50, 60, 70, 80, 90, and 100 formed from nitinol wire by the method of this invention. The objects have various shapes that are difficult to form by conventional methods.

Object 10 is an open ended substantially cylindrical tubular mesh of trained material. Object 20 is the structure described in FIG. 1. Object 30 is an on-axis end view of the structure described in FIG. 2. Object 40 is a closed spherical structure of trained material. Object 50 is a side view of the structure described in FIG. 2. Object 60 is a structure similar to that described in FIG. 6. Object 70 is the structure described in FIG. 3. Object 80 is a side view of a structure similar to that described in FIG. 2 with smaller openings at the ends of the trained structure. Object 90 is the structure described in FIG. 5. Object 100 is a mesh of material trained into closed ended cylinder.

Figure 8:
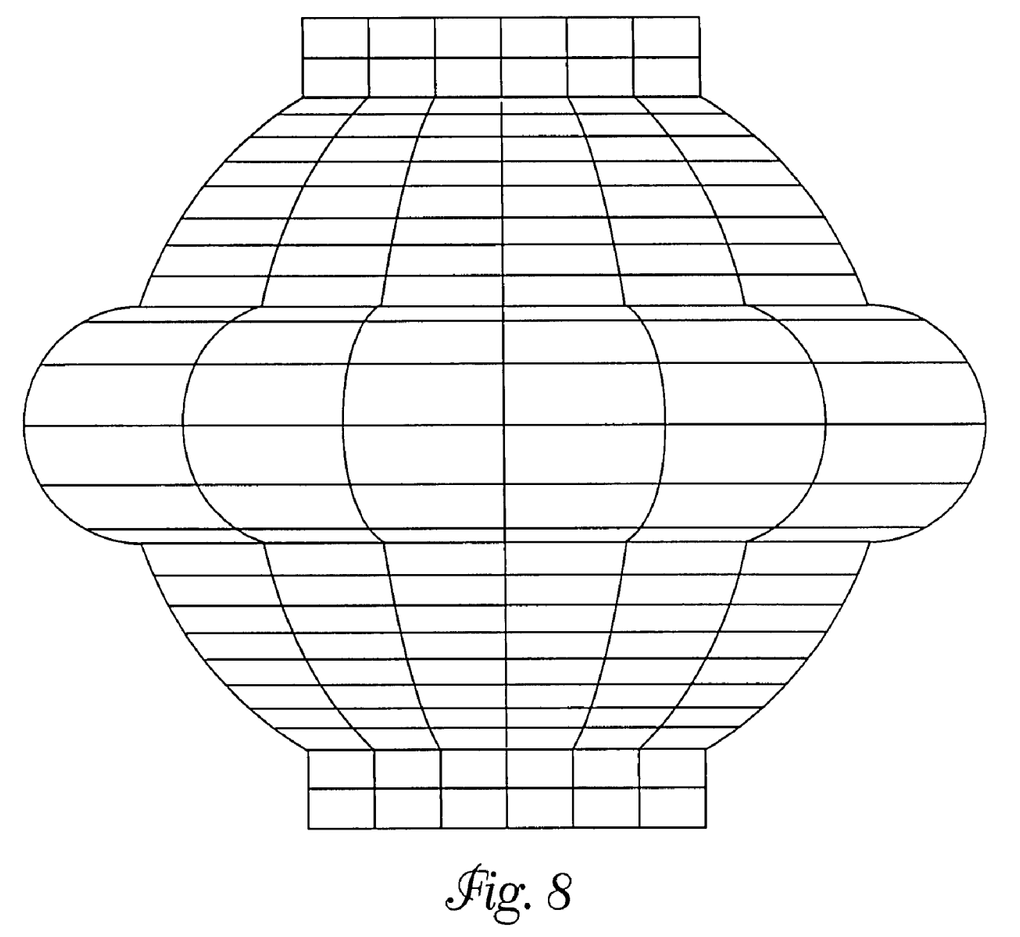
FIGS. 8 to 12 show plans and dimensions for a complicated nitinol wire structure that can be trained by the method of the invention.
Figure 9:
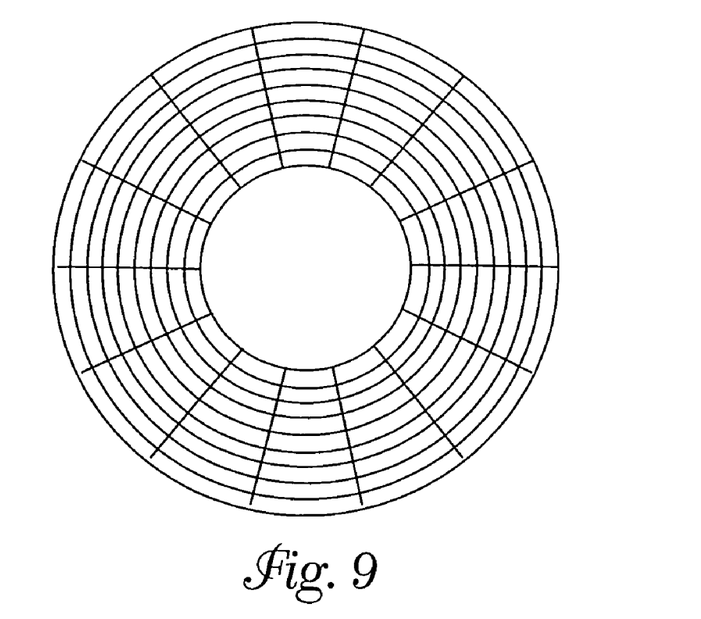

FIG. 8 shows a side view of a complex cylindrical shape formed by the method of this invention, and FIG. 9 is a top view. This cylinder is open at both bottom and top, and illustrates a shape for which the process of this invention is advantageous, i.e., larger in its center section than at the top and bottom. FIG. 10 shows the dimensions of this complex cylinder. The axial radius R1 is 0.5 inch (1.27 cm), the diameter a of the top opening is 0.527 inch (1.34 cm), the length e is 1.05 inch (2.67 cm), and the width b is 1.25 inches (3.17 cm). Segment h has a radius R2 of 0.156 inch (0.4 cm). The top end segment c is 0.1 inch (0.25 cm) long and the body segment d is 0.85 inch (2.16 cm) long.

In this embodiment, at least one sacrificial piece of the mold remains with the substance-covered nitinol, particularly that piece or those pieces that would otherwise be difficult to remove after the heat treating process. In the case of FIG. 1, there would be one internal piece that would otherwise be difficult to remove after the heat treating process, so this would be the piece that would remain in this preferred embodiment, while the external piece or pieces would be removed before the heat treating process. For this reason, the following description will differentiate between the internal and external pieces. However, one skilled in the art would realize other types of mold pieces could exist-besides internal and external—and that some external pieces could remain with the nitinol and thus be sacrificial while some internal pieces could be removed, without deviating from the spirit of the invention.

Figure 11:
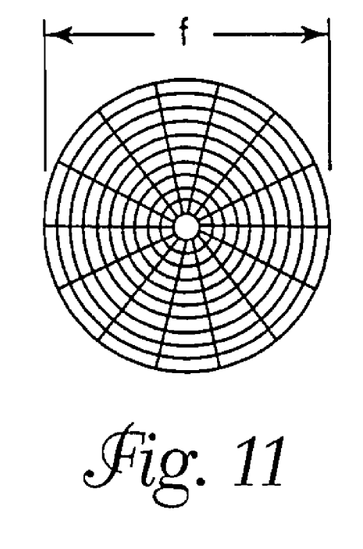
Figure 12:
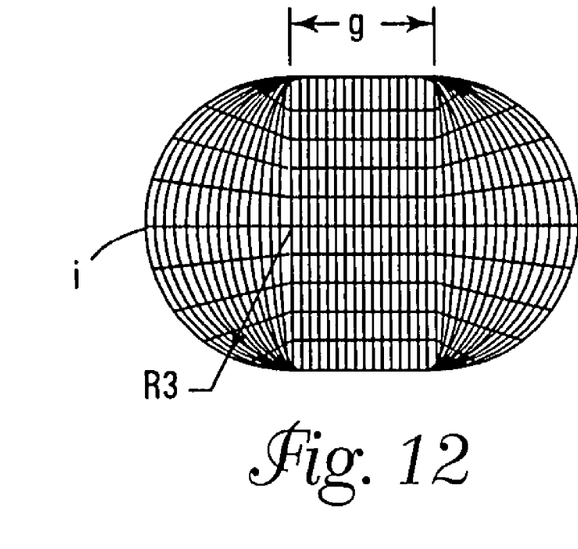

FIG. 11 shows a top view of a sphere, having diameter f of 0.5 inch (1.27 cm), and FIG. 12 shows a side view of an ovoid, in which opening g is 0.25 inch (0.64 cm) wide, and a segment i has a radius R3 of 0.25 inch (0.64 cm).

Figure 13:
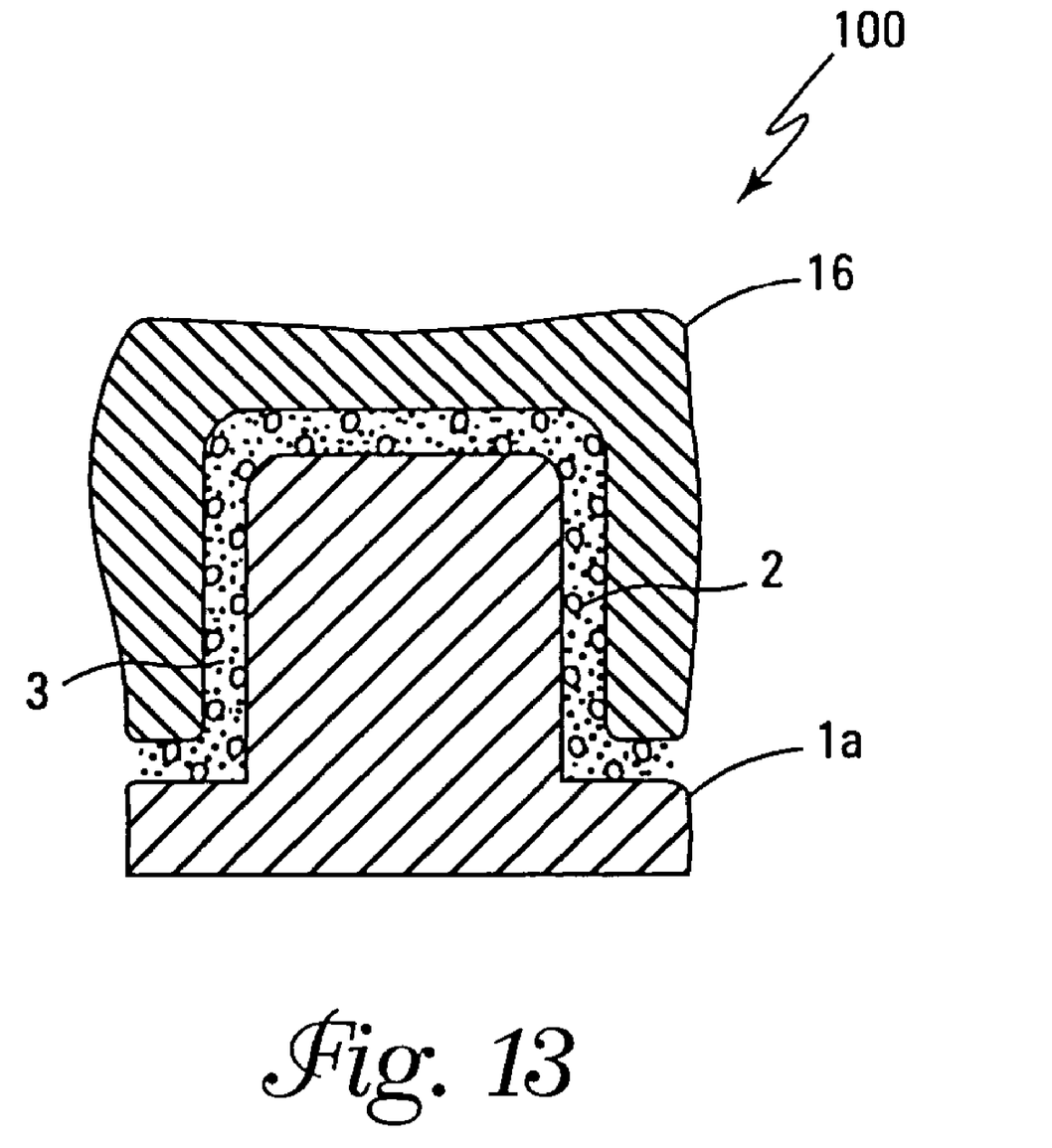
FIG. 13 is a sectional view of a mold assembly suitable for use in the method of the invention.

FIG. 13 is a cross-sectional view of a mold assembly 100 which can be used in the method of this invention. Mold assembly 100 includes portions 1a and 1b which contain trainable material 2 such as nitinol wire and heat resistant substance 3.

In a preferred embodiment, the mold is created from polyethylene by the injection molding process. The nitinol is formed as described previously and the heat-resistant substance is applied and hardened as described previously. The external piece or pieces of the mold are then removed from the substance-coated nitinol while at least one internal sacrificial piece remains. The nitinol—coated with the heat-resistant substance and enclosing at least one internal mold piece—is then subjected to the heat treatment. The polyethylene internal mold piece, which vaporizes and burns (i.e., pyrolyzes) at a temperature lower than the training temperature of nitinol, will then burn. The heat treatment continues until all remains of the sacrificial mold have vaporized or combusted, or until enough of the mold has vaporized or combusted to allow the remains of the mold to pass through the exit of the shape's enclosure. The substance-coated nitinol is then subjected to the cooling process and substance-removal process as discussed previously. It will be apparent to one skilled in the art that the mold can be made of many possible substances that vaporize or burn at a temperature lower than the training temperature of nitinol. For example, other types of plastics could be used.

In another embodiment, the sacrificial mold is created from a substance that can be easily dissolved, broken, or chemically reacted with another substance, as previously discussed. For example, the sacrificial mold could be created of the same substance as the heat-resistant substance and could be removed at the same time, and through the same process, as the heat-resistant substance. For example, the mold could be created from plaster of paris, and the nitinol could be coated with plaster of paris according to the process described. After the heat treating process, both the internal sacrificial mold piece and the heat-resistant substance could be removed at substantially the same time by dissolving them in water. They could also be removed at substantially the same time by pulverizing them with a powerful high-frequency sound wave. In addition, the sacrificial mold could be created of a substance different than the heat-resistant substance, with their respective removal processes either the same or different.

Figure 14A:
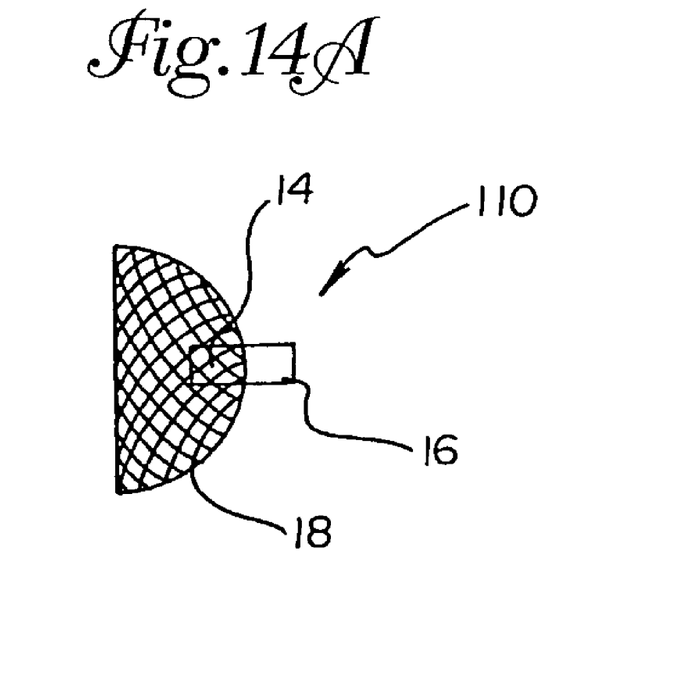
FIGS. 14A and 14B are side and cross-sectional views, respectively, of a nitinol medical device formed by the method of this invention.
Figure 14B:
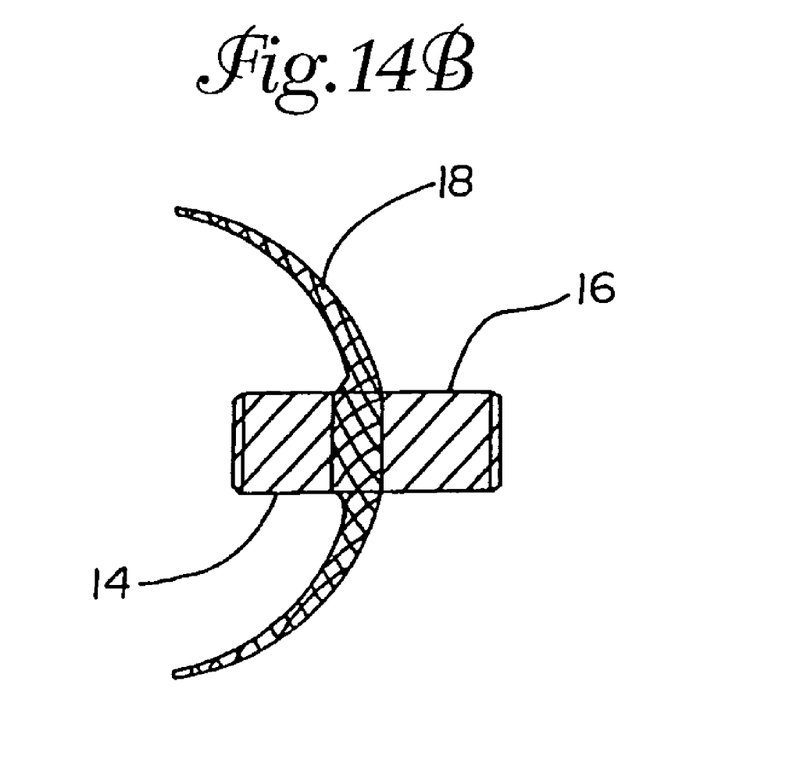

The method of this invention can be used to train a trainable material for many different applications. One such application is shown in FIGS. 14A and 14B which show a filter device for use in a lumen of a human body such as a vessel in the vascular system. FIG. 14A is a side view of device 110 and FIG. 14B is a cross-sectional view. Device 110 is comprised of a cylinder of trainable mesh material 18 trained into a bell like shape with one end open and one end closed. The ends of the trainable material are contained within elements 14 and 16 which may be solid or tubular. In use device 110 is carrier by an elongate support member which may be a guide wire. One of the elements 14 and 16 is fixed to the support member and the other slides over the support member. This configuration allows the device to be delivered through the lumen in a reduced diameter configuration when elements 14 and 16 are spaced apart and to be expanded in the lumen by moving elements 14 and 16 closer together.

While a number of preferred embodiments of the present invention have been described, it should be understood that various changes, adaptations, and modifications may be made therein without departing from the spirit of the invention and the scope of the appended claims. As used herein and in the following claims, articles such as "the," "a," and "an" can connote the singular or plural.

What is claimed is:

1. A method of training a trainable material, comprising:
    forming the trainable material into a desired shape about a mold, the desired shape of the trainable material including a substantially enclosed volume which substantially encompasses the mold;
    applying a heat-resistant substance to the trainable material, said heat-resistant substance being in a non-solid form that hardens after application and is capable of restraining the material in the desired shape;
    removing the mold;
    heating the trainable material to a temperature and for a time sufficient for the trainable material to retain the desired shape;
    cooling the trainable material; and
    removing the heat-resistant substance from the trainable material.

2. A method as claimed in claim 1, wherein the trainable material permanently retains the shape.

3. A method as claimed in claim 1, wherein the trainable material comprises a nickel titanium alloy.

4. A method as claimed in claim 3, wherein the nickel titanium alloy is a nitinol alloy.

5. A method as claimed in claim 1, wherein the heat-resistant substance comprises plaster of paris, concrete, a ceramic, a paint, a glue or a varnish.

6. A method as claimed in claim 1, wherein the temperature is between about 450° C. and about 600° C.

7. A method as claimed in claim 1, wherein the heat-resistant substance remains in a solid form at the temperature.

8. A method as claimed in claim 1, wherein in the heating step, the time is between one second and ten minutes.

9. A method as claimed in claim 1, wherein the step of cooling the trainable material comprises cooling the trainable material with a gas.

10. A method as claimed in claim 9, wherein the gas is air.

11. A method as claimed in claim 10, wherein the air is compressed.

12. A method as claimed in claim 1, wherein the step of cooling the trainable material comprises cooling the trainable material with a liquid.

13. A method as claimed in claim 12, wherein the liquid is water.

14. A method as claimed in claim 1, wherein the mold comprises a plastic, a metal or a ceramic.

15. A method as claimed in claim 14, wherein the mold has been created by injection molding.

16. A method as claimed in claim 15, wherein the plastic is an ethylene.

17. A method as claimed in claim 1, wherein the step of removing the heat-resistant substance comprises dissolving the heat-resistant substance in a dissolving substance.

18. A method as claimed in claim 17, wherein the dissolving substance is water.

19. A method as claimed in claim 1, wherein the step of removing the heat-resistant substance comprises breaking the heat-resistant substance or chemically reacting the heat-resistant substance with a reacting substance.

20. A method as claimed in claim 19, wherein the breaking of the heat-resistant substance comprises vibrating the heat-resistant substance.

21. A method according to claim 1, wherein the trainable material comprises a braid.

22. A method according to claim 1, wherein the trainable material comprises a metallic braid.

23. A method according to claim 22, wherein the metallic braid comprises a nickel-titanium alloy.

24. A method according to claim 23, wherein the nickel-titanium alloy comprises Nitinol.

25. A method according to claim 1, wherein the trainable material comprises wire, wire mesh, braided wire, a sheet, a tube, or a form that can be manipulated into the desired shape.

26. A method according to claim 1, wherein at least a portion of the trainable material remains free of the heat-resistant substance.

27. A method according to claim 1, wherein the heat-resistant substance is applied by dipping, pouring or spraying.

28. A method according to claim 1 wherein the step of removing the mold comprises disassembling or destroying the mold.

29. A method of training a trainable material, comprising:
    providing a mold of a desired shape;
    forming the trainable material into the desired shape with the use of the mold, the desired shape of the trainable material including a substantially enclosed volume with at least a hole or a core through which the mold in a shape of the substantially enclosed volume cannot exit;
    applying a heat-resistant substance to the trainable material formed in the desired shape, the heat-resistant substance being in a non-solid form that hardens after application and is capable of holding the trainable material in the desired shape;
    removing the mold;
    heating the trainable material in the desired shape to a temperature and for a time sufficient for the trainable material to retain the desired shape;
    cooling the trainable material; and
    removing the heat-resistant substance from the trainable material.

30. A method as claimed in claim 29, further comprising removing at least a part of the mold prior to heating the trainable material.

31. A method as claimed in claim 29, wherein the trainable material permanently retains the shape.

32. A method as claimed in claim 29, wherein at least a part of the mold is retained after applying the heat resistant substance and the at least the part is pyrolyzed during the heating of the trainable material.

33. A method as claimed in claim 29, wherein the trainable material comprises a nickel titanium alloy.

34. A method as claimed in claim 33, wherein the nickel titanium alloy is a nitinol alloy.

35. A method as claimed in claim 29, wherein the heat-resistant substance comprises plaster of paris, concrete, a ceramic, a paint, or a glue.

36. A method as claimed in claim 29, wherein in the heating step, the temperature is between about 450° C. and about 600° C.

37. A method as claimed in claim 29, wherein in the heating step, the heat-resistant substance remains in a solid form at the temperature.

38. A method as claimed in claim 29, wherein in the heating step, the time is between one second and ten minutes.

39. A method as claimed in claim 29, wherein the step of cooling the trainable material comprises cooling the trainable material with a gas or a liquid.

40. A method as claimed in claim 39, wherein the gas is air.

41. A method as claimed in claim 40, wherein the air is compressed.

42. A method as claimed in claim 39, wherein the liquid is water.

43. A method as claimed in claim 29, wherein the mold has at least two pieces and further wherein the step of heating the trainable material comprises heating at least one piece of the mold.

44. A method as claimed in claim 43, wherein the at least one piece vaporizes at a vaporization temperature below the temperature.

45. A method as claimed in claim 44, wherein the at least one piece completely vaporizes during the time.

46. A method as claimed in claim 44, wherein the at least one piece comprises a plastic.

47. A method as claimed in claim 46, wherein the at least one piece has been created by injection molding.

48. A method as claimed in claim 46, wherein the plastic is an ethylene.

49. A method as claimed in claim 43, further comprising the step of removing the at least one piece from the trainable material.

50. A method as claimed in claim 49, wherein the step of removing the piece comprises dissolving the at least one piece in a mold dissolving substance, breaking the at least one piece or chemically reacting the piece with a mold reacting substance.

51. A method as claimed in claim 50, wherein the mold dissolving substance is water.

52. A method as claimed in claim 49, wherein the breaking of the piece comprises vibrating the piece.

53. A method as claimed in claim 49, wherein the step of removing the heat-resistant substance and removing the at least one piece occur at substantially the same time.

54. A method as claimed in claim 29, wherein the step of removing the heat-resistant substance comprises dissolving the heat-resistant substance in a dissolving substance, breaking the heat-resistant substance or chemically reacting the heat-resistant substance with a reacting substance.

55. A method as claimed in claim 54, wherein the dissolving substance is water.

56. A method as claimed in claim 54, wherein the breaking of the heat-resistant substance comprises vibrating the heat-resistant substance.

57. A method as claimed in claim 29, wherein the mold comprises plastic, metal or ceramic.

58. A method according to claim 29, wherein the trainable material comprises a braid.

59. A method according to claim 29, wherein the trainable material comprises a metallic braid.

60. A method according to claim 59, wherein the metallic braid comprises a nickel-titanium alloy.

61. A method according to claim 60, wherein the nickel-titanium alloy comprises Nitinol.

62. A method according to claim 29, wherein the trainable material comprises wire, wire mesh, braided wire, a sheet, a tube, or a form that can be manipulated into the desired shape.

63. A method according to claim 29, wherein at least a portion of the trainable material remains free of the heat-resistant substance.

64. A method according to claim 29, wherein the heat-resistant substance is applied by dipping, pouring or spraying.

65. A method according to claim 29 wherein the step of removing the mold comprises disassembling or destroying the mold.

* * * * *